(12) United States Patent
Fischer et al.

(10) Patent No.: US 9,681,933 B2
(45) Date of Patent: *Jun. 20, 2017

(54) BRUSH HEAD FOR A TOOTHBRUSH AND METHOD FOR PRODUCING THE BRUSH HEAD

(71) Applicant: TRISA HOLDING AG, Triengen (CH)

(72) Inventors: Franz Fischer, Triengen (CH); Peter Gross, Sempach (CH)

(73) Assignee: TRISA HOLDING AG, Kantonsstrasse (CH)

( * ) Notice: Subject to any disclaimer, the term of this patent is extended or adjusted under 35 U.S.C. 154(b) by 643 days.

This patent is subject to a terminal disclaimer.

(21) Appl. No.: 14/089,310

(22) Filed: Nov. 25, 2013

(65) Prior Publication Data

US 2014/0082866 A1    Mar. 27, 2014

Related U.S. Application Data

(63) Continuation of application No. 13/690,824, filed on Nov. 30, 2012, now Pat. No. 8,621,699, which is a (Continued)

(51) Int. Cl.
*A46B 13/02* (2006.01)
*A61C 17/34* (2006.01)
(Continued)

(52) U.S. Cl.
CPC ............ *A61C 17/222* (2013.01); *A46B 7/06* (2013.01); *A46B 9/025* (2013.01); *A46B 9/026* (2013.01); *A46B 9/028* (2013.01); *A46B 9/04* (2013.01); *A46B 9/045* (2013.01); *A46B 9/06* (2013.01); *A46B 13/02* (2013.01); *A46B 13/023* (2013.01); *A46B 15/0002* (2013.01); *A46B 15/0032* (2013.01); *A46D 1/00* (2013.01); *A46D 1/0276* (2013.01); *A46D 1/0284* (2013.01);
(Continued)

(58) Field of Classification Search
CPC .. A46B 13/02; A46B 15/0002; A61C 17/3418
See application file for complete search history.

(56) References Cited

U.S. PATENT DOCUMENTS 1,924,152 A   8/1933   Coney et al.
1,981,657 A   11/1934  Miller
(Continued)

FOREIGN PATENT DOCUMENTS

BR   9 604 425 A   3/1998
BR   9 915 580 A   8/2001
(Continued)

OTHER PUBLICATIONS

Mar. 24, 2010 Office Action issued in U.S. Appl. No. 12/010,500.
(Continued)

*Primary Examiner* — Randall Chin
(74) *Attorney, Agent, or Firm* — Oliff PLC (57) ABSTRACT

The brush head of the toothbrush has filaments that are pointed at one end and led through clearances in the bristle carrier. These filaments have a length of about 10-20 mm. The tips of the pointed filaments produce a height profile other than that of a plane and the ends of the pointed filaments that are remote from the tips are melted.

25 Claims, 10 Drawing Sheets

Related U.S. Application Data continuation of application No. 11/826,442, filed on Jul. 16, 2007, now Pat. No. 8,341,792, which is a continuation-in-part of application No. 11/255,990, filed on Oct. 24, 2005, now Pat. No. 7,419,225, which is a continuation of application No. PCT/CH03/00263, filed on Apr. 22, 2003.

(51) Int. Cl.

| | | |
|---|---|---|
| *A61C 17/22* | (2006.01) | |
| *A46B 7/06* | (2006.01) | |
| *A46B 9/02* | (2006.01) | |
| *A46B 9/04* | (2006.01) | |
| *A46B 9/06* | (2006.01) | |
| *A46B 15/00* | (2006.01) | |
| *A46D 1/00* | (2006.01) | |

(52) U.S. Cl.
CPC .......... *A61C 17/22* (2013.01); *A61C 17/3418* (2013.01); *A61C 17/3481* (2013.01); *A46B 2200/1066* (2013.01); *Y10S 15/05* (2013.01)

(56) References Cited

U.S. PATENT DOCUMENTS

| | | |
|---|---|---|
| 3,103,027 A | 9/1963 | Birch |
| 3,183,538 A | 5/1965 | Hubner |
| 4,225,994 A | 10/1980 | Stoltz |
| 4,277,862 A | 7/1981 | Weideman |
| 4,646,381 A | 3/1987 | Weihrauch |
| 4,679,272 A | 7/1987 | Florence |
| 4,979,782 A | 12/1990 | Weihrauch |
| 5,305,489 A | 4/1994 | Lage |
| 5,500,975 A | 3/1996 | Sano |
| 5,533,227 A | 7/1996 | Ito et al. |
| 5,823,633 A | 10/1998 | Weihrauch |
| 5,991,957 A | 11/1999 | Watanabe |
| 6,021,538 A | 2/2000 | Kresner et al. |
| 6,088,869 A | 7/2000 | Kaneda et al. |
| 6,090,488 A | 7/2000 | Kweon |
| 6,202,241 B1 | 3/2001 | Hassell et al. |
| 6,290,302 B1 | 9/2001 | Boucherie |
| 6,370,726 B1 | 4/2002 | Kini et al. |
| 6,371,294 B1 | 4/2002 | Blaustein et al. |
| 6,406,099 B2 | 6/2002 | Boucherie |
| 6,546,586 B2 | 4/2003 | Cho |
| 2004/0068811 A1 | 4/2004 | Fulop et al. |
| 2004/0117930 A1 | 6/2004 | Townley et al. |
| 2005/0091769 A1 | 5/2005 | Jimenez et al. |

FOREIGN PATENT DOCUMENTS

| | | |
|---|---|---|
| CH | 421 049 | 9/1966 |
| DE | 27 28 672 A1 | 1/1979 |
| DE | 28 20 437 A1 | 7/1979 |
| DE | 33 23 169 A1 | 1/1985 |
| DE | 90 12 603 | 2/1992 |
| DE | 295 20 230 A1 | 2/1996 |
| DE | 44 41 985 A1 | 5/1996 |
| DE | 199 42 147 A1 | 3/2001 |
| EP | A 0 596 633 | 5/1994 |
| JP | A-11-75939 | 3/1999 |
| JP | 2001-178542 * | 7/2001 |
| WO | WO 00/30495 A1 | 6/2000 |
| WO | WO 01/28452 A1 | 4/2001 |

OTHER PUBLICATIONS

May 21, 2010 Office Action issued in U.S. Appl. No. 11/826,442.
Feb. 9, 2011 Office Action issued in U.S. Appl. No. 11/826,442.
Feb. 9, 2011 Office Action issued in U.S. Appl. No. 12/010,500.
Jul. 27, 2011 Office Action issued in U.S. Appl. No. 11/826,442.
Jul. 29, 2011 Office Action issued in U.S. Appl. No. 12/010,500.
Mar. 16, 2012 Office Action issued in U.S. Appl. No. 11/826,442.
Aug. 29, 2012 Notice of Allowance issued in U.S. Appl. No. 11/826,422.

* cited by examiner

BRUSH HEAD FOR A TOOTHBRUSH AND METHOD FOR PRODUCING THE BRUSH HEAD

This application is a Continuation Application of U.S. patent application Ser. No. 13/690,824 filed Nov. 30, 2012 now U.S. Pat. No. 8,621,699 issued on Jan. 7, 2014, which is a Continuation Application of U.S. patent application Ser. No. 11/826,442 filed on Jul. 16, 2007 now U.S. Pat. No. 8,341,792 issued on Jan. 1, 2013, which is a Continuation-in-Part of U.S. patent application Ser. No. 11/255,990 filed on Oct. 24, 2005 now U.S. Pat. No. 7,419,225 issued on Sep. 2, 2008, which is a Continuation Application of PCT Application No. PCT/CH2003/00263 filed in Switzerland on Apr. 22, 2003. The disclosure of the prior applications is hereby incorporated by reference herein in their entirety.

BACKGROUND

The disclosure relates to a brush head for an electric or manual toothbrush and to a method for producing such a brush head.

Electric toothbrushes usually have a handle, in which a motor is accommodated, and a generally exchangeable brush head. A brush head with a bristle carrier which can be driven in a rotationally movable manner is known for example from DE-U 295 20 230. An electric toothbrush of which the brush head is made to vibrate is disclosed by WO 01/28452. Furthermore, electric toothbrushes of which the brush heads perform a pivoting movement about their longitudinal axis in the manner of a rocker are also known, for example from CH 421 049. Known electric toothbrushes have a brush head which is provided with clusters of conventional bristles. These are rounded off at their end to avoid injuries.

Manual toothbrushes with a bristle arrangement which entirely comprises pointed filaments are known for example from EP-A 0 596 633 and DE-U 90 12 603. The pointed filaments serve for the handling or cleaning of fine structures in the surface of the tooth, for example fine cracks, which cannot be effectively treated with conventional cylindrical bristles. Furthermore, thanks to the narrower tips, the pointed filaments penetrate better into the spaces between the teeth and clean them better. Electric toothbrushes with pointed bristles are not known.

However, pointed bristles react poorly to mechanical abrasion in the region of the tip. Under excessive mechanical loading, the tips of these bristles break and may, on the one hand, no longer bring about the cleaning effect and, on the other hand, entail the risk of injuring the gums by the edges and corners that are produced when they break off.

SUMMARY

The invention is therefore based on the object of further improving the cleaning effect of toothbrushes with pointed bristles and optimizing the service life of the bristles with minimal potential for injury of the gums.

The object is achieved by a brush head for a toothbrush that includes filaments that are pointed at one end, are led through clearances in a bristle carrier and have a length of about 10 to 20 mm, the tips of the pointed filaments producing at least in certain regions a height profile other than that of a plane, and the ends of the pointed filaments that are remote from the tips being melted. A production method includes leading filaments that are pointed at one end and have a length of about 10 to 20 mm through clearances in a bristle carrier, the tips of the pointed filaments producing at least over certain regions a height profile other than that of a plane, and melting the ends of the pointed filaments that are remote from the tips. Advantageous developments of the invention are provided by the dependent claims, the description and the drawings.

The invention is based on the finding that the cleaning effect of pointed filaments can be optimally used with minimal wear if the path which the pointed filaments cover during use as intended is restricted. This possibility exists in the case of electric or manual toothbrushes on which the brush head or the bristle carrier, and with it the bristles, is set in motion and generally only a minimal additional manual cleaning movement is performed. In the case of electric toothbrushes, the path of the pointed filaments or the tips that is covered during use can therefore be controlled and restricted well by the arrangement of the filaments on the bristle carrier. According to the invention, the pointed filaments are arranged on the bristle carrier in such a way that, during the operation of the electric toothbrush, their tips cover at most a predetermined maximum path $d_{max}$. The rest of the bristle carrier may be provided with conventional bristles and/or further cleaning elements, for example soft-elastic elements. Conventional bristles and/or further cleaning elements may also be arranged between the pointed filaments.

The high-frequency motion of the pointed filaments produces an optimum cleaning performance. The restriction of the path which the tips cover has the effect of minimizing the wear of the bristles, so that the risk of injury to the gums is also kept low.

With preference, the maximum path $d_{max}$ of the tips is 5 mm, with particular preference 3 mm. These distances correspond to the typical dimensions of relatively large spaces between the teeth or of the teeth. If these maximum values are taken as a basis, the bristles move within the structures in the set of teeth. This allows in particular the finest fissures on the tooth surface and the interdental spaces to be reached well. It is also possible to reduce what is known as a "whiplash effect" when brushing over the spaces between the teeth perpendicularly to their alignment. In the case of the "whiplash effect", the intrinsic flexibility of the pointed filaments causes them to bend when they meet obstacles, such as the transition between two teeth, and lash forward like a whip when there is further movement, making the filaments undergo considerable stress.

The filaments may be pointed at one end or at both ends. They may also be colored, at least in the region of the tip. The color variation also provides the user with a visible indication of the wear of the brush, for example if the color washes out over time.

BRIEF DESCRIPTION OF THE DRAWINGS

The invention is explained in more detail below with reference to the drawings, in which, purely schematically:

FIG. 12 shows a brush head with clusters of bristles according to FIG. 10a;

FIG. 14b is an enlarged view of a section of the receiving tank as shown in FIG. 14a; FIG. 15b is an enlarged view of a section of FIG. 15a.

DETAILED DESCRIPTION OF EMBODIMENTS

Figure 1A:
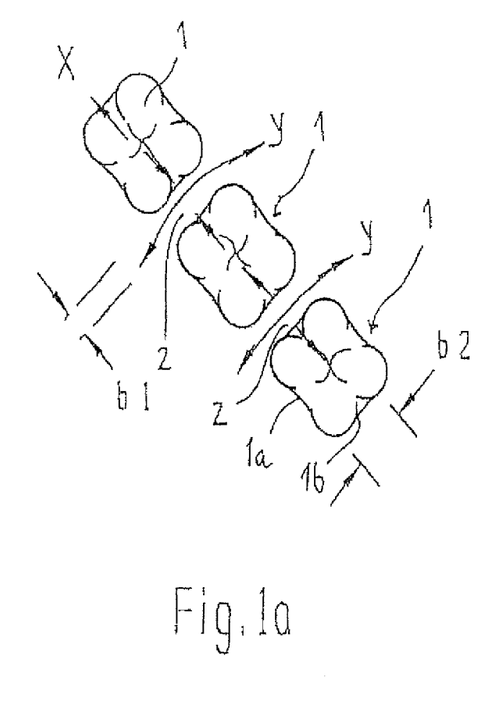
FIGS. 1a, 1b respectively show three teeth in side view and plan view to illustrate the desired movements.
Figure 1B:
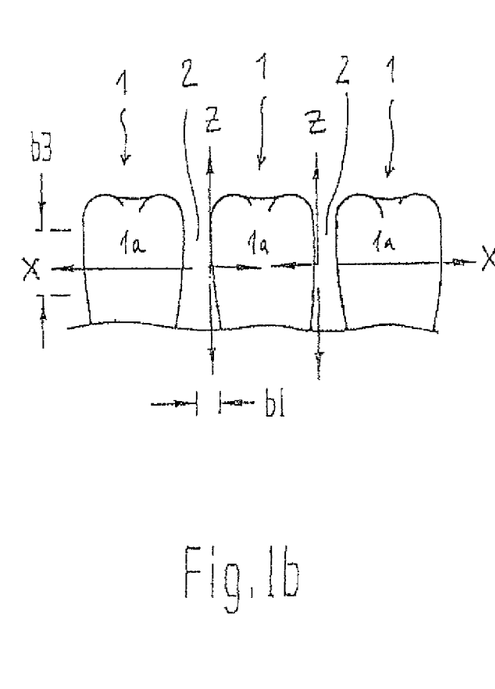

FIGS. 1a, b show three teeth 1, standing in a row of teeth, with interdental spaces 2 lying in between, respectively in side view and plan view. Examples of brush heads 3 with pointed filaments 5 are provided by the other figures.

With pointed filaments 5, preferably small movements along the row of teeth in the direction x and rather greater movements transversely thereto, i.e. in the direction Y, are performed in the plane of the teeth or in the direction Z perpendicular to the plane of the teeth. Excessive movements along the x direction are to be avoided, since they are accompanied by great mechanical loading of the pointed filaments 5 (whiplash effect). Consequently, the desired movements of the pointed filaments 5 extend over the entire width b1 of the interdental spaces 2 and over a strip of the width b2 and b3, respectively, along the flanks 1a, 1b of the teeth. The width b1 is typically about 2 mm, the width b2, b3 in each case about 5 mm.

In order to achieve an improved cleaning effect in comparison with manual cleaning, the brush head 3 is driven in such a way that the pointed filaments 5 achieve more than 1000 cleaning movements per minute, but preferably more than 5000 movements. In the case of manual cleaning, significantly fewer than 1000 movements are achieved during the entire cleaning process. For each movement, the tip 5a of a pointed bristle covers a distance d with respect to the stationary set of teeth (i.e. without overlaying a movement that may possibly be performed manually). In order not to subject the pointed filaments 5 to excessive loading under this high-frequency back and forth motion on the tooth surfaces and in particular when changing between tooth surface 1a, 1b and spaces between the teeth, the path d of the tips 5a of the filaments 5 is less than a predetermined maximum path $d_{max}$, which is preferably 3 mm. These values correspond approximately to the size of large spaces 2 between the teeth, which can consequently be optimally cleaned without damaging the tips 5a. The control and restriction of the movements of the tips 5a has the effect of reducing the risk of injuries to the gums.

In an advantageous development, the maximum path $d_{max}$ of the tips 5a depends on the direction of movement, the maximum path $d_{max,long}$ in the longitudinal direction L of the brush head 3 preferably being less than the maximum path $d_{max,trans}$ transversely thereto. The longitudinal direction L of the brush head 3 corresponds during use approximately to the direction x of the row of teeth in which the movements of the bristles are preferably to be restricted because of the tooth-to-tooth transition and the accompanying loading of the bristles. This makes allowance for the geometry of the set of teeth and allows a movement along the spaces 2 between the teeth, i.e. in the Y and Z directions, with a greater deflection than transversely thereto. With preference, $d_{max,long}$ is 3 mm (X direction) and $d_{max,trans}$ is 5 mm (Y, Z directions).

FIGS. 2-4 and 5a-c show various examples of brush heads with a bristle arrangement of conventional bristles 6 and pointed filaments 5. The bristles 5, 6 are respectively arranged in clusters 5', 6' on a bristle carrier 4. The clusters 6' of conventional bristles 6 are symbolized by an empty circle and the clusters 5' of pointed filaments 5 are symbolized by a circle with a dot.

Figure 2:
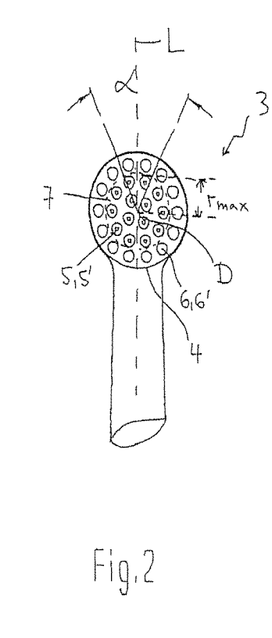
FIG. 2 shows a brush head with a bristle carrier rotatably connected to it, with conventional bristles and pointed filaments.

In the case of the brush head 3 represented in FIG. 2, the bristle carrier 4 is connected to the brush head 3 such that it can rotate back and forth about an axis of rotation D running perpendicularly to the bristle carrier 4. For this purpose, a suitable drive is present (not represented here). During operation, a maximum angle of rotation α is achieved. The pointed filaments 5 are arranged on the bristle carrier in such a way that the following applies for the maximum distance $r_{max}$ of their exit points on the bristle carrier from the axis of rotation D: $r_{max}=d_{max} \cdot 180°:(\pi\alpha)$, where $d_{max}$ is the maximum path mentioned at the beginning. By approximation (distance between the points of inflection instead of length of the arc), the following applies: $r_{max}=d_{max}:(2 \sin(\alpha/2))$. Preferably, $d_{max}=3$ mm.

Devices with angles of rotation of up to 70° are currently on the market. The diameter of the brush head 3 is generally less than 20 mm. The movement of the tips 5a increases with the radius or the distance from the axis of rotation. The following table gives some values for the path, calculated in dependence on the angle of rotation and the radius. The figures for the path that are shown with a * belong to the pairs of radius/angle-of-rotation values that are permissible according to the invention for $d_{max}=3$ mm ($d_{max}=$distance between the points of inflection).

| Radius (mm) | α = 10° | α = 20° | α = 30° | α = 40° | α = 50° | α = 60° | α = 70° |
|---|---|---|---|---|---|---|---|
| 1 | 0.2* | 0.3* | 0.5* | 0.7* | 0.8* | 1.0* | 1.1* |
| 2 | 0.3* | 0.7* | 1.0* | 1.4* | 1.7* | 2.0* | 2.3* |
| 3 | 0.5* | 1.0* | 1.6* | 2.1* | 2.5* | 3.0* | 3.4 |
| 4 | 0.7* | 1.4* | 2.1* | 2.7* | 3.4 | 4.0 | 4.6 |
| 5 | 0.9* | 1.7* | 2.6* | 3.4 | 4.2 | 5.0 | 5.7 |
| 6 | 1.0* | 9.1* | 3.1 | 4.1 | 5.1 | 6.0 | 6.9 |
| 7 | 1.2* | 2.4* | 3.6 | 4.8 | 5.9 | 7.0 | 8.0 |
| 8 | 1.4* | 7.8* | 4.1 | 5.5 | 6.8 | 8.0 | 9.2 |
| 9 | 1.6* | 3.1 | 4.7 | 6.2 | 7.6 | 9.0 | 10.3 |
| 10 | 1.7* | 3.5 | 5.2 | 6.8 | 8.5 | 10.0 | 11.5 |

The table shows that, in the case of small angles of rotation, in principle the entire brush head 3 can be provided with pointed filaments 5 and that, in the case of large angles of rotation, only a central segment 7 should be provided with pointed filaments 5.

Figure 3:
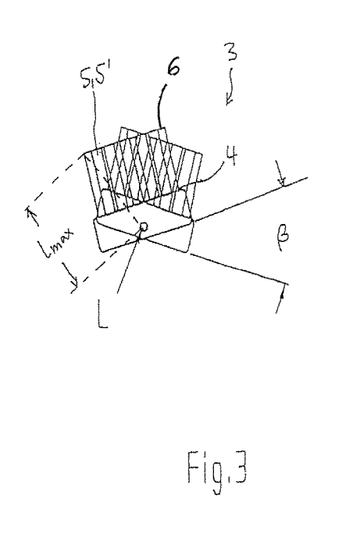
FIG. 3 shows a brush head with a bristle carrier pivotable about the longitudinal axis, with conventional bristles and pointed filaments.

FIG. 3 shows a brush head 3, which is pivoted about its longitudinal axis L during operation, so that the brush head 3 performs a rocking sideward motion. The brush head 3 thereby passes over an angle β. The following applies for the maximum distance $l_{max}$ of the tips of the pointed filaments from the longitudinal axis L: $l_{max}=d_{max}\cdot 180°:(\pi\beta)$ or $l_{max}=d_{max}:(2\sin(\beta/2))$ (distance between the points of inflection), where $d_{max}$ is the maximum path mentioned at the beginning. Preferably, $d_{max}=3$ mm.

In connection with pointed filaments 5, the rocking sideward motion is particularly appropriate. With this type of toothbrush, during use the pointed filaments 5 move along the interdental spaces 2. The direction of movement that is less desired for the bristles and the gums is excluded for the pointed filaments 5. In the case of this movement, the maximum path covered by the tips should likewise be less than 3 mm. The angle of rotation can consequently be fixed on the basis of the following table in dependence on the distance of the tips from the pivot axis. The figures for the path that are shown with a * belong to the pairs of distance/pivoting-angle values that are permissible according to the invention for $d_{max}=3$ mm. In the case of an average distance of 12 mm, the angle of rotation of the brush head should be chosen to be not greater than 15°.

| Distance (mm) | β = 10° | β = 15° | β = 20° | β = 25° | β = 30° | β = 35° |
| --- | --- | --- | --- | --- | --- | --- |
| 9 | 1.6* | 2.3* | 3.1 | 3.9 | 4.7 | 5.4 |
| 10 | 1.7* | 2.6* | 3.5 | 4.3 | 5.2 | 6.0 |
| 11 | 1.9* | 2.9* | 3.8 | 4.8 | 5.7 | 6.6 |
| 17 | 2.1* | 3.1 | 4.2 | 5.2 | 6.2 | 7.2 |
| 13 | 2.3* | 3.4 | 4.5 | 5.6 | 6.7 | 7.8 |
| 14 | 2.4* | 3.7 | 4.9 | 6.1 | 7.2 | 8.4 |
| 15 | 2.6* | 3.9 | 5.2 | 6.5 | 7.8 | 9.0 |

Figure 4:
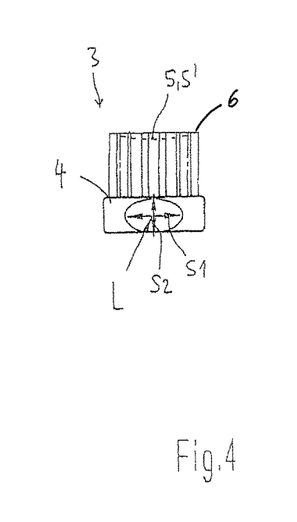
FIG. 4 shows a brush head with a vibrating bristle carrier with conventional bristles and pointed filaments.

FIG. 4 shows purely schematically a brush head 3, which vibrates in two directions S1, S2 transversely to the longitudinal direction L. In the case of this variant of movement, the brush head geometry has less influence on the deflection of the conventional bristles 6 and pointed filaments 5. The size of the deflection can be determined by choice of the electric current, motor and/or vibration generators. The direction of the deflection can be influenced by a special construction of the brush handle, for example stiffening in the vertical direction, and additional damping measures. Since the deflection of the brush head 3, and with it the tips of the pointed filaments 5, preferably follows the interdental spaces 2, the toothbrush is preferably intended to have a greater lateral deflection in the direction S1 than a vertical deflection in the direction S2. Deflections of less than 3 mm here also produce a very gentle action and stimulation of the gums.

Figures 5A, 5B:
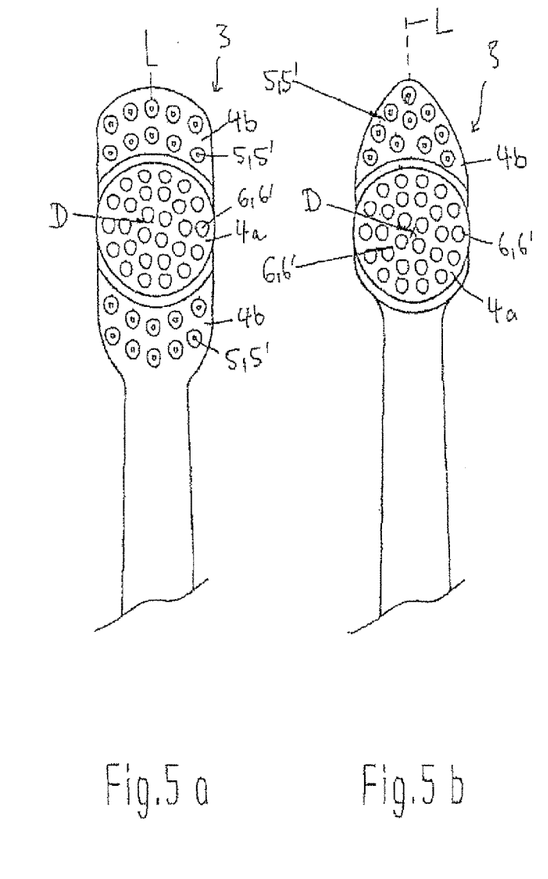
FIGS. 5a-c show a brush head with a multipart bristle carrier.
Figures 5C, 6A, 7:
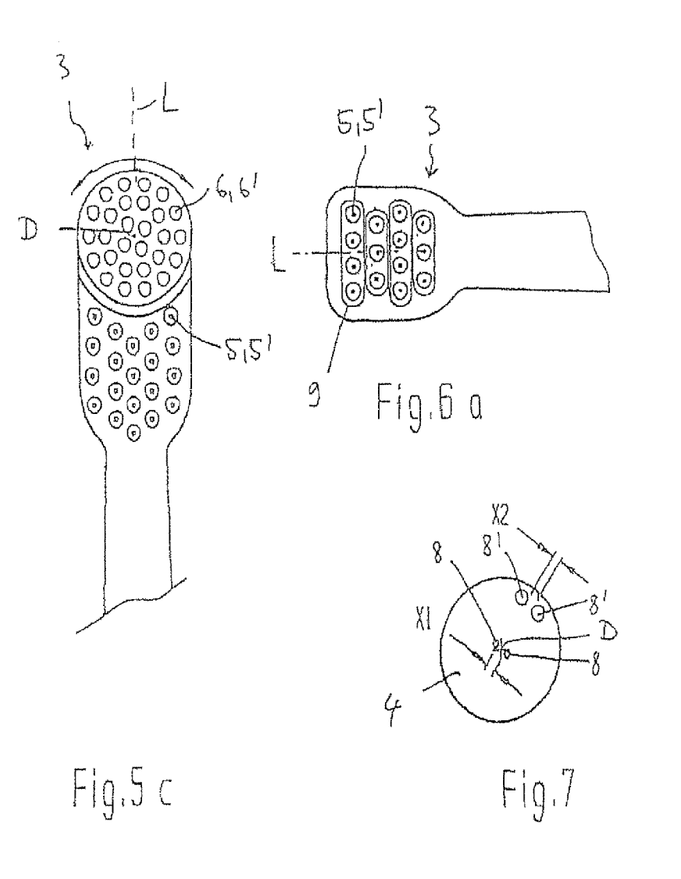
FIGS. 6a-d show preferred arrangements of clusters of pointed filaments on a brush head.
FIG. 7 shows a bristle carrier with clusters of pointed filaments.

FIGS. 5a-c show brush heads 3 in the case of which a rotational movement is combined with other types of movement. If a mechanical movement, for example rotation, is performed with an electric toothbrush, vibration is also produced in any event. In the present examples, the bristle carrier 4 is of a multipart form. A round, first carrier element 4a is connected to the brush head 3 rotatably about the axis of rotation D (cf. FIG. 2). It is provided with conventional bristles 6. At least one further carrier element 4b is firmly connected to the brush head 3 and provided with pointed filaments 5. Under rotation of the part 4a, it is made to vibrate. In FIG. 5a, this further carrier element 4b is in front of and behind the rotating carrier element 4a in the longitudinal direction L; in FIG. 5b, it is only behind it and in FIG. 5c it is only in front of it. The moved carrier element 4a with conventional bristles 6 undertakes the surface cleaning and the co-vibrating, only indirectly mechanically moved carrier element 4b with the pointed filaments 5 undertakes the interdental cleaning and the cleaning of very small structures. Instead of rotating the first carrier element 4a, it may also be pivoted about the longitudinal axis.

FIGS. 6a-d show examples of the arrangement of the pointed filaments 5 on the bristle carrier 4. The pointed filaments 5 are first grouped together in clusters 5'. In the present case, these are circular in cross section, but may also have some other shape, for example as represented in FIGS. 10a-e. In the case of the brush head 3 according to FIG. 6a, the clusters 5' are grouped together in rows 9, which run transversely to the longitudinal direction L. This arrangement is used with preference in the case of bristle carriers 4 which can pivot about the longitudinal axis L or vibrate in this direction, since the rows 9 coincide there with the running direction of the clusters 5'. In the case of the example from FIG. 6b, the bristle clusters 5' are arranged on arcs of a circle 10. This arrangement is used with preference in the case of rotating bristle carriers 4. There are two inner circles of bristle clusters 5' with pointed filaments 5, the maximum radius of which is $r_{max}$. In both cases, the active region of the pointed filaments 5 can consequently be spatially restricted well.

FIG. 6c shows an example of a bristle arrangement with mixed clusters 5', 6' of pointed filaments 5 and conventional bristles 6 on a round bristle carrier 4 with a radius $r_{max}$. The mixed bristle arrangement has the advantage that the pointed filaments 5 have more freedom of movement and, in spite of bending on the tooth structures, cannot become jammed in one another during use. In principle, the pointed filaments 5 should be given more freedom of movement than the conventional bristles 6. In particular at the outer limits, i.e. for arrangements in which the bristle tips cover approximately the maximum distance $d_{max}$, such a mixture with conventional bristles is advantageous.

FIG. 6d shows a bristle arrangement in which the clusters 5' of pointed filaments 5 are arranged in segments 11 in the form of arcs of a circle. This arrangement corresponds substantially to FIG. 6b and is likewise suitable for rotating brushes.

Instead of arranging bristle clusters 5' with a round cross section as described in groups (rows, circles, segments), bristle clusters 5' with a correspondingly adapted cross section may also be used (see FIGS. 11a-e).

In order that the pointed filaments 5 can move freely and the interdental spaces 2 are not clogged, the individual clusters 8 are preferably spaced sufficiently apart from one another. Since, in the case of certain embodiments, the tips cover different distances in dependence on their location on the bristle carrier 4, the minimum hole spacing x between neighboring clusters 8 is fixed in dependence on the path covered. FIG. 7 shows an example of a rotating bristle carrier 4, of which only a centrally arranged pair of bristle clusters 8 and a peripherally arranged further pair of bristle clusters 8' are shown for the sake of overall clarity. The minimum spacings x1 near the axis of rotation D are smaller than the minimum spacings x2 further away from the axis of rotation D.

Figure 6:
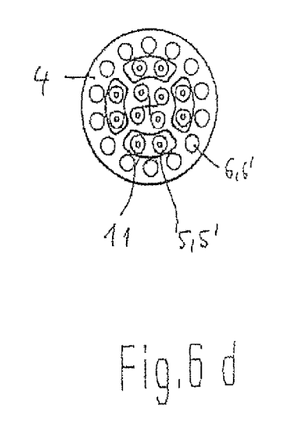
Figures 6, 8:
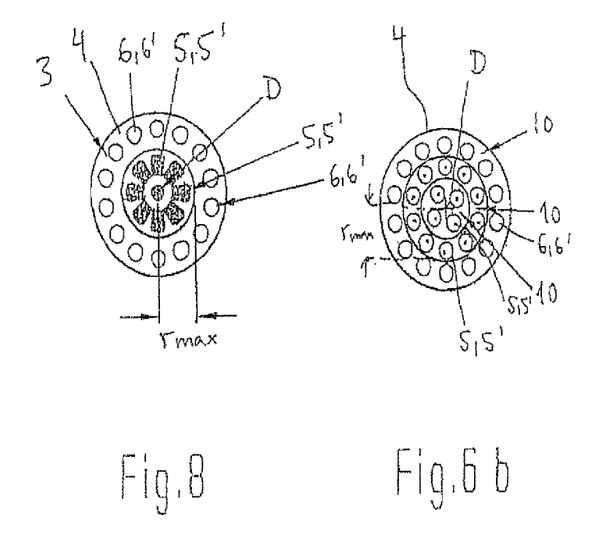
FIG. 8 shows a bristle carrier with clusters of pointed filaments and conventional bristles.

Since, in the case of certain embodiments it is only appropriate to arrange the pointed filaments at a suitable position on the surface of the brush head, other types of filaments can be used at the positions which are not suitable. Conventionally rounded-off bristles, which consist for example of polyester PBT or polyamide PA, may be used in particular for the surface cleaning of the tooth surface. If a massaging effect of the gums is additionally required, soft rubber-elastic elements in the form of bristles, lamellae or other formations of thermoplastic elastomer TPE may be additionally molded or inserted. FIG. 8 shows an example of a bristle carrier 4 with such a mixed bristle arrangement comprising pointed filaments 5 within a central area with a radius $r_{max}$ and peripherally arranged conventional bristle clusters 6.

Figure 9A:
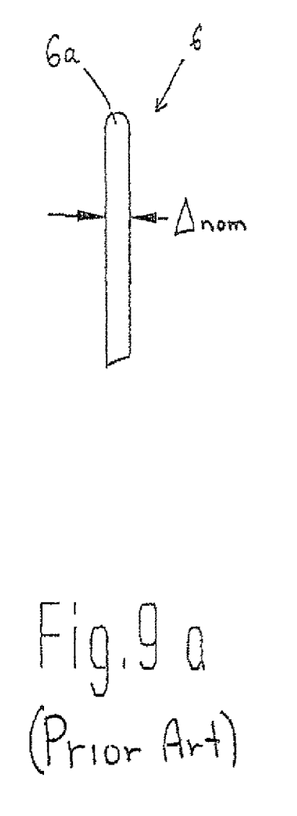
FIGS. 9a, 9b respectively show a conventional bristle and a pointed bristle.
Figure 9B:
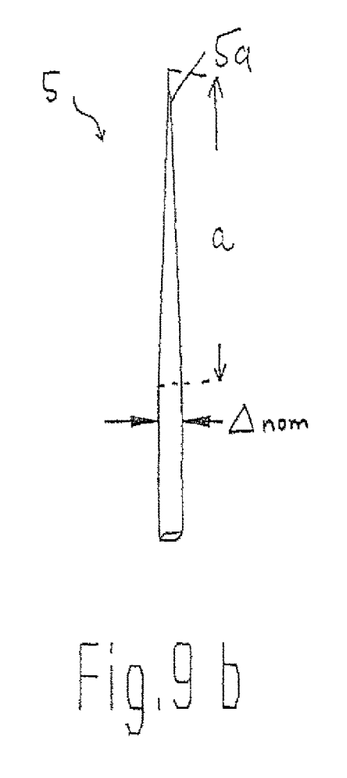

FIGS. 9*a*, *b* explain the dimensioning of the conventional bristles 6 and the pointed filaments 5. The conventional bristles 6 outlined in FIG. 9*a* have over their length a substantially constant nominal diameter $\Delta_{nom}$, (diameter at the thickest point of the bristle), which is for example 0.15 to 0.25 mm. The tip 6*a* of the bristle is rounded off.

In order to minimize the potential for injury in the case of toothbrushes with high-frequency motions and maximize their lifetime, special requirements are imposed on the geometry and the nature of the pointed filaments 5. The pointed filaments 5 outlined in FIG. 9*b* likewise have a constant diameter over a region of their length, for example likewise a nominal diameter of 0.15-0.25 mm. Toward the tip 5*a*, the bristle 5 tapers, beginning at a distance a from the tip 5*a*. Measured from the tip 5*a*, the diameter at the corresponding point corresponds for example to the following values:

| Distance | % of the nominal diameter | |
|---|---|---|
| (mm) | Mean value | Tolerance range |
| 0.1 | 8% | 5-15% |
| 1 | 25% | 15-35% |
| 2 | 45% | 30-60% |
| 3 | 60% | 50-80% |
| 4 | 75% | 60-90% |
| 5 | 80% | 70-90% |
| 6 | 85% | >75% |
| 7 | 90% | >80% |

In order to achieve adequate flexibility of the filaments, their length from where they leave the brush head is chosen to be between 7 and 13 mm. In order to ensure adequate stability of the individual filaments under high-frequency motion, over 75% of the nominal diameter is left over a large part of the length. The table presented above shows that the pointing of the filaments predominantly takes place over the last 4 to 5 mm. With this configuration, the tip 5*a* can optimally reach the smallest fissures and interdental spaces 2 with adequate filament stability.

For the pointed bristles, polyamide is preferably used, or else polyester (PBT). The pointing process is based on the reduction of the diameter by means of a chemical process. Depending on the length of time for which the bristle remains in the chemical substance, the plastic decomposes and the diameter is reduced. In this way, the shape of the point can be influenced.

Figure 10A:
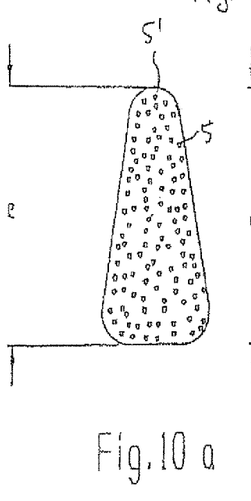
FIGS. 10a-e show clusters of pointed filaments with various shapes.
Figure 10B:
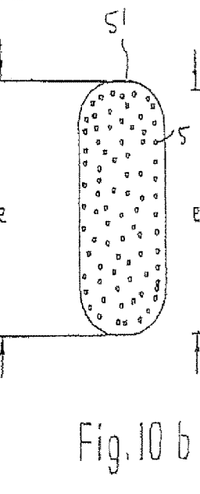
Figure 10C:
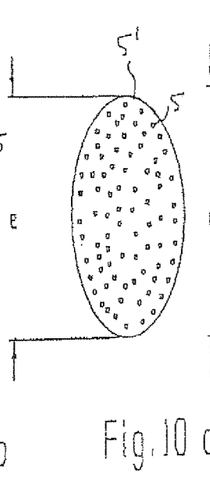
Figure 10D:
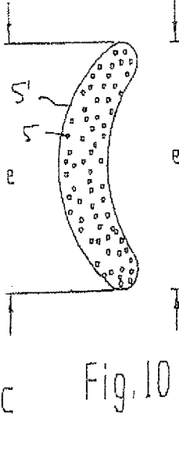
Figure 10E:
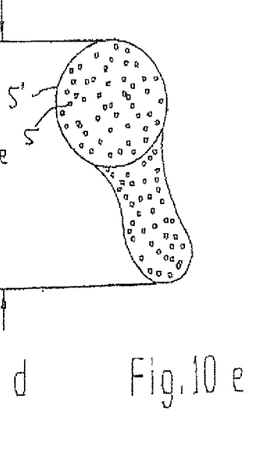
Figure 12:
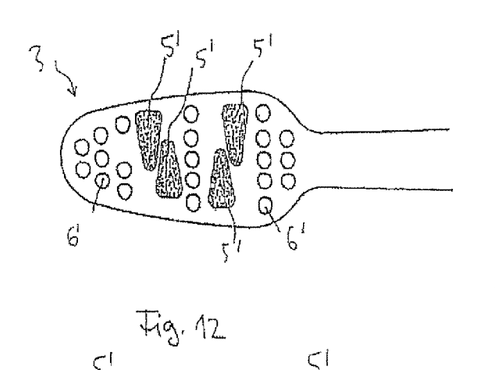

FIGS. 10*a-e* show examples of the shape of clusters 5' of pointed filaments 5. Such a cluster 5' does not necessarily have to have a round shape. Substantially triangular (FIG. 10*a*), substantially rectangular (FIG. 10*b*), elliptical (FIG. 10*c*), arcuate (FIG. 10*d*) or other shapes (FIG. 10*e*) come into consideration. The elongate shapes according to FIGS. 10*a-c* are appropriate in particular for pivotable toothbrushes and may be used instead for the arrangement of round bristle clusters in rows (cf. FIG. 12, in which a mixed bristle arrangement of normal bristle clusters 6' with round cross section and clusters 5' of pointed filaments 5 with the shape represented in FIG. 10*a* is shown). The shape shown in FIG. 10*d* is particularly advantageous for rotating toothbrushes.

Figure 13A:
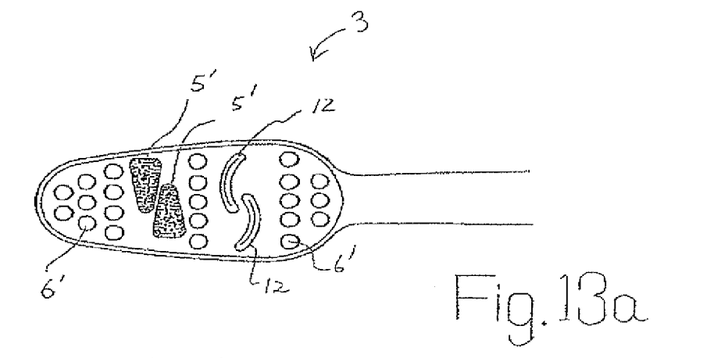
FIGS. 13a, 13b show a brush head with clusters of bristles with soft elements.
Figure 13B:
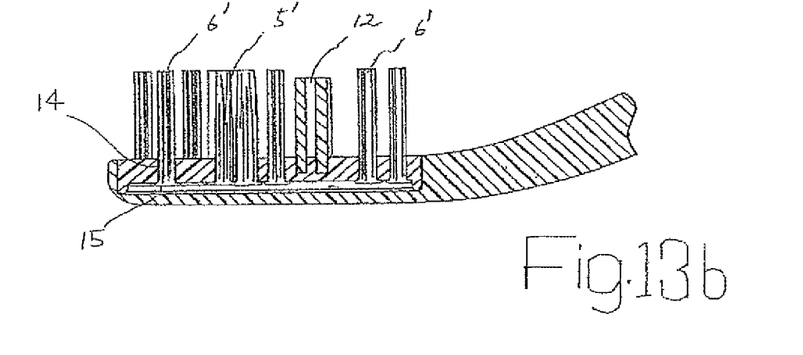

FIGS. 13*a-b* show another embodiment of a mixed bristle arrangement of normal bristle clusters 6' with round cross section and clusters 5' of pointed filaments 5. In this embodiment, a set of the clusters 5' is replaced by a pair of soft rubber-elastic elements 12.

The greatest extent e is preferably approximately 3 mm and consequently corresponds to a large interdental spacing. If too many filaments are grouped together in each cluster 5', this can cause unnecessary stiffening of the individual filaments 5 and make penetration into the interdental spaces 2 more difficult. A cluster 5' therefore preferably contains fewer than 80, with particular preference fewer than 50, pointed tips 5*a* of the filaments 5. In this case, depending on the production technique, each filament may have one or two pointed tips 5*a*. Certain filaments also have a round tip and a pointed tip 5*a*.

Figure 10F:
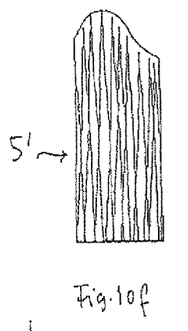
FIGS. 10f, 10g show clusters of pointed filaments with various profiles.
Figure 10G:
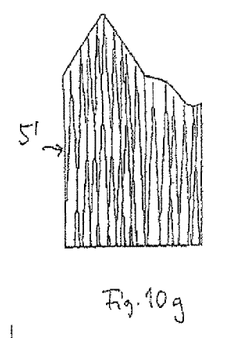
Figure 11A:
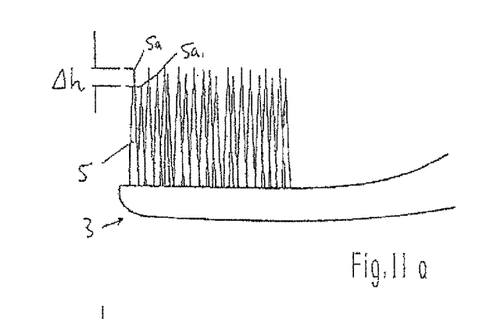
FIGS. 11a-e show brush heads in side view with various profiles of the pointed filaments.
Figure 11B:
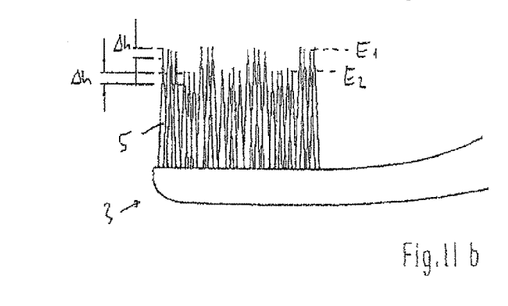
Figure 11C:
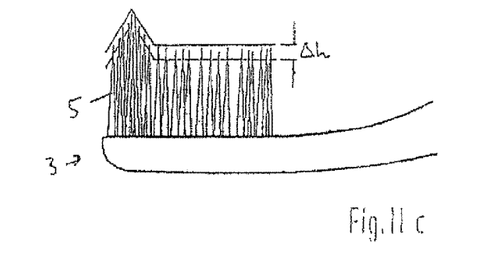
Figure 11D:
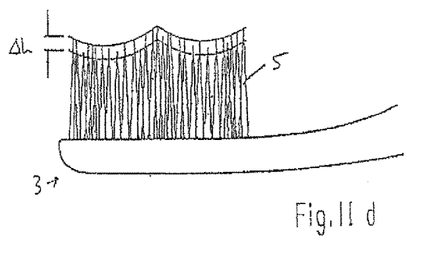
Figure 11E:
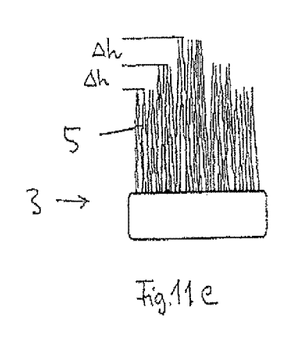

FIGS. 10*f+g* show examples of the height profile of the bristle clusters 5' from FIGS. 11*d* and 11*e*, respectively. Such non-constant height profiles are realized with preference by the AFT or IMT method.

FIGS. 11*a-e* show brush heads 3 in side view, in the case of which the tips 5*a* of the pointed filaments 5 form different profiles. FIGS. 11*a-d* relate to pivotable brush heads, FIG. 11*e* to a rotating brush head.

For fabrication reasons, the flat profile shown in FIG. 11*a* can be produced most simply. In this case, just one basic filament length is used, adopting conventional punching technology. Approximately 80% of the filament ends are positioned within the height range Δh of 4 mm in latitude. Different filament lengths within these limits are desired to a certain extent, since they consequently ensure easier interdental penetration than in the case of an exactly equal length, as is produced when cutting conventional bristles. Individual, prominently projecting filaments should be avoided, however, since they entail the risk of injuring the gums, in particular under high-frequency motion.

FIG. 11*b* shows a brush head in the case of which a profile shape deviating from a plane is produced by means of conventional punching technology with two different basic lengths of the pointed bristles. Usually, both ends of the filaments are pointed. The latter are bent in a U-shaped manner to create bristles. For this reason, the pointed bristles cannot be cut, and with this technology there is a limitation to different planes, here planes E1 and E2. Within the planes E1, E2, height variations are in turn possible within the height range Δh of approximately 4 mm. There is greater freedom with filaments pointed at one end.

If, for the reasons already mentioned, different filament types are combined, the pointed filaments 5 for the interdental cleaning are preferably longer than conventionally rounded-off bristles or massaging elements. The different types of bristles are preferably used in the bristle carrier in place of the other respective type or types of bristles. Alternatively, the bristle carriers 4 could be of a multipart form, separately provided with bristles and subsequently joined together.

For the production of the brush heads 3 according to the invention, the AFT (Anchor Free Tufting) method or IMT (In Mold Tufting) method is appropriate in particular. The AFT method is described for example in EP-A 0 972 464. The IMT method is described for example in EP-A 0 795 711 and EP-A 0 346 646. Unlike in the case of conventional tufting, the pointed filaments 5 are in this case only pointed at one end when they are fed to the AFT or IMT machine.

Figure 14A:
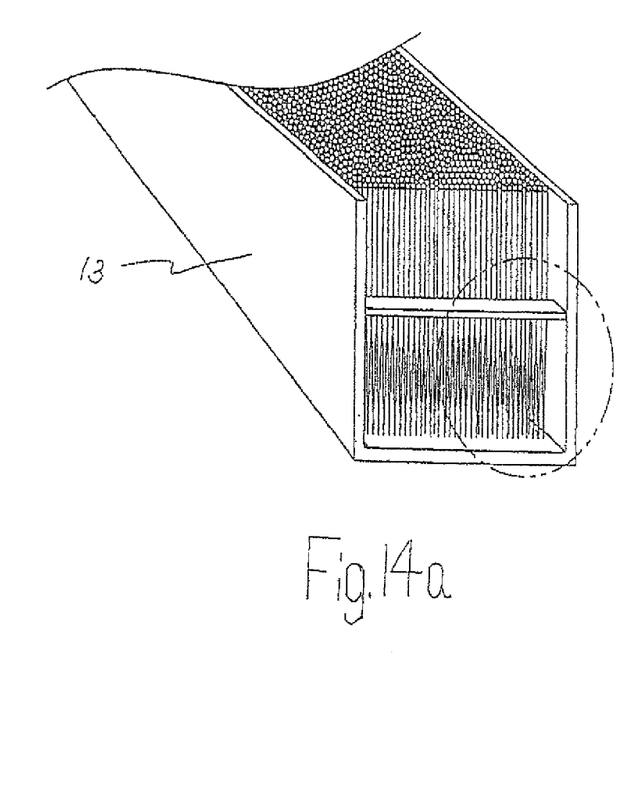
FIG. 14a shows a receiving tank filled with pointed filaments.
Figure 14B:
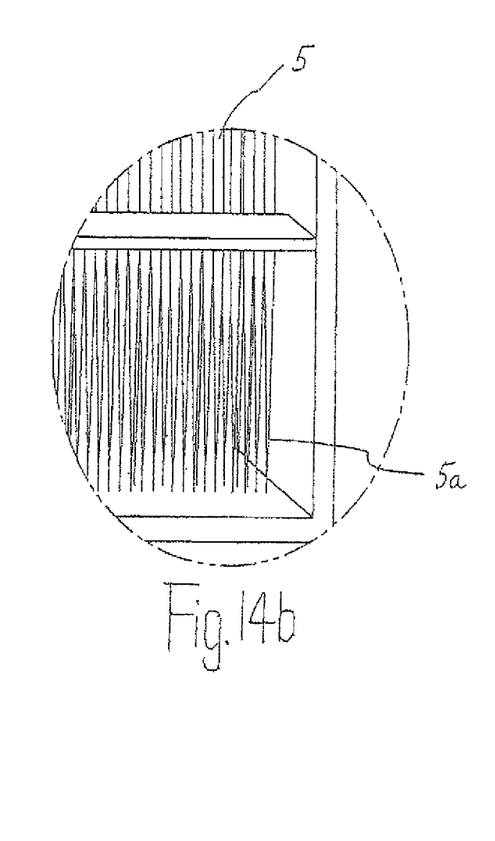
Figure 15A:
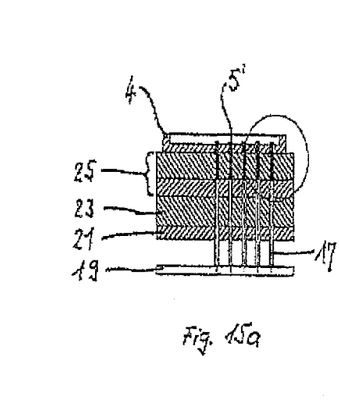
FIG. 15a shows pushing means for pushing clusters of filaments through a bristle carrier and further parts off an AFT machine.
Figure 15B:
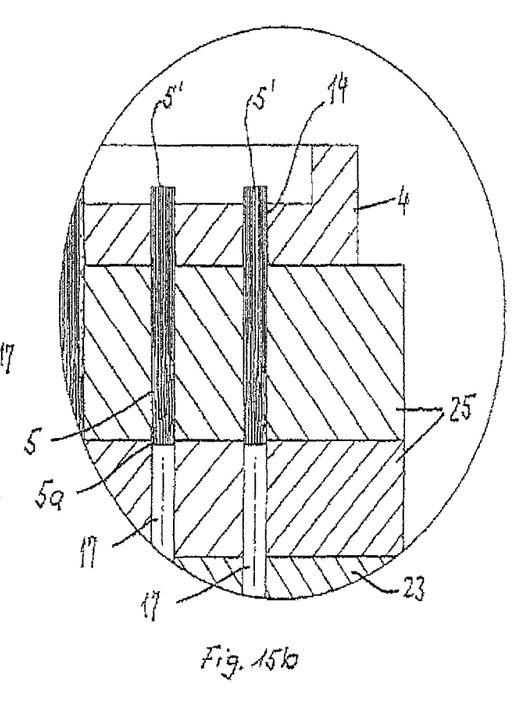

The length of the filaments is between 10 and 20 mm. As shown in FIGS. 14a, 14b, the filaments 5 are preferably inserted into the receiving tank 13 with the tips 5a downward. There is consequently no need for later reorientation within the AFT or IMT machine. The filaments 5 are pushed by the pushing means 17 on the pointed side 5a through the bristle carrier 4 (in the case of IMT through the transporting inserts) as shown in FIGS. 15a, 15b. For this purpose, as also shown in FIG. 13b, the bristle carrier has clearances 14 for the bristles. The non-pointed side is cut and, as known, subsequently melted to form a melted end 15. If the bristle carrier is not in one piece with the brush head, the two parts are subsequently connected to each other, preferably by means of ultrasonic welding. The FIGS. 15a, 15b further show a support 19 for the pushing means 17, a guidance plate 21, a carrier means 23 and a filament guidance 25 of an AFT machine as disclosed in EP 0 972 464.

The AFT or IMT method makes simplified production of the pointed filaments possible, since they only have to be pointed at one end. Furthermore, by corresponding configuration of the pushing means, the individual clusters are profiled, for example for better interdental penetration. Examples of this are shown in FIGS. 11c-e and also in FIGS. 10f+g (profiling of the individual clusters). This is not possible with the conventional tufting technology. Since the filaments are cut after the profiling, only one filament length has to be provided. The bristles can be cut to the desired length. By contrast with this, in the case of conventional tufting technology, a number of material lengths have to be used to create a topology other than that of a plane.

The AFT and IMT methods consequently have great advantages for the production of the toothbrushes according to the invention, since a largely unrestricted shape of the bristle clusters is made possible. This allows the path covered by the tips during use to be controlled particularly well. The production method can also be advantageously used for the production of manual toothbrushes.

What is claimed is:

1. An electric toothbrush comprising a brush head with a bristle carrier which can be set in motion and in which bristles are anchored, the bristle carrier being capable of performing a pivoting movement about a pivoting axis running substantially in the longitudinal direction of the brush head, with a maximum pivoting angle ($\beta$), wherein at least part of the bristles are pointed filaments, which are arranged on the bristle carrier in such a way that the maximum distance ($l_{max}$) of the tips of the pointed filaments from the pivoting axis is $l_{max}=d_{max}\cdot 180°:(\pi\beta)$ or $l_{max}=d_{max}:(2\sin(\beta/2))$ and wherein during the operation of the electric toothbrush, the tips of the pointed filaments cover at most a path $d_{max}=3$ mm.

2. The electric toothbrush according to claim 1, wherein the brush head is driven in such a way that the bristles perform at least 1000 movements per minute.

3. The electric toothbrush according to claim 1, wherein the pointed filaments have a maximum diameter of 0.15 to 0.25 mm and a length, measured from the exit point on the bristle carrier of 7 to 13 mm, the diameter being greater than 75% of the nominal diameter up to a distance of 5 to 6 mm from the tip and becoming smaller as the distance becomes less.

4. The electric toothbrush according to claim 1, wherein the pointed filaments are arranged in clusters.

5. The electric toothbrush according to claim 4, wherein the clusters have a maximum width of about 3 mm.

6. The electric toothbrush according to claim 4, wherein the clusters are arranged on the bristle carrier one behind the other in a direction of movement.

7. The electric toothbrush according to claim 1, wherein at least 80% of the pointed filaments have a length, measured from the exit point on the bristle carrier, from the interval [L, L+4 mm], where L is a predetermined length.

8. The electric toothbrush according to claim 1, wherein in addition to the pointed filaments, conventional bristles are provided, the pointed filaments being longer than the conventional bristles.

9. The electric toothbrush according to claim 1, wherein the pointed filaments are colored, at least in the region of the tip.

10. The electric toothbrush according to claim 1, wherein in addition to the pointed filaments, the bristle carrier comprises soft-elastic cleaning elements.

11. The electric toothbrush according to claim 1, further comprising a handle.

12. A method for producing an electric toothbrush according to claim 1, the method comprising providing the bristle carrier with pointed filaments and optionally conventional bristles at predetermined points.

13. The method according to claim 12, wherein the bristle carrier is provided with bristles by the AFT or IMT method.

14. The method according to claim 13, wherein pointed filaments and optionally normal bristles are led through clearances in the bristle carrier in such a way that their tips assume a predetermined height profile and in that the remote ends are subsequently cut and melted.

15. The method according to claim 14, wherein the bristle carrier is inserted into a prepared clearance in the brush head and is connected to the latter.

16. An electric toothbrush comprising a brush head with a bristle carrier which can be set in motion and in which bristles are anchored, the bristle carrier being capable of performing a pivoting movement about a pivoting axis running substantially in the longitudinal direction of the brush head, with a maximum pivoting angle, and wherein at least part of the bristles are pointed filaments, which are arranged on the bristle carrier in such a way that during the operation of the electric toothbrush the tips of the filaments cover at most a path $d_{max}=5$ mm and wherein the brush head is driven in such a way that the bristles perform at least 1000 movements per minute.

17. An electric toothbrush comprising a brush head with a bristle carrier which can be set in motion and in which bristles are anchored, the bristle carrier being capable of performing a pivoting movement about a pivoting axis running substantially in the longitudinal direction of the brush head, with a maximum pivoting angle, and wherein at least part of the bristles are pointed filaments, which are arranged on the bristle carrier in such a way that during the operation of the electric toothbrush the tips of the filaments cover at most a path $d_{max}=5$ mm and wherein the pointed filaments have a maximum diameter of 0.15 to 0.25 mm and a length, measured from the exit point on the bristle carrier of 7 to 13 mm, the diameter being greater than 75% of the nominal diameter up to a distance of 5 to 6 mm from the tip and becoming smaller as the distance becomes less.

18. An electric toothbrush comprising a brush head with a bristle carrier which can be set in motion and in which bristles are anchored, the bristle carrier being capable of performing a pivoting movement about a pivoting axis running substantially in the longitudinal direction of the brush head, with a maximum pivoting angle, and wherein at least part of the bristles are pointed filaments, which are arranged on the bristle carrier in such a way that the distance of the tips of the pointed filaments from the pivoting axis is between 9 and 12 mm and wherein the pivoting angle is not greater than 15°.

19. The electric toothbrush according to claim 18, wherein during the operation of the electric toothbrush, the tips of the pointed filaments cover at most a path $d_{max}=3$ mm.

20. The electric toothbrush according to claim 18, wherein the pointed filaments are colored, at least in the region of the tip.

21. The electric toothbrush according to claim 18, wherein the brush head is driven in such a way that the bristles perform at least 1000 movements per minute.

22. The electric toothbrush according to claim 18, wherein at least 80% of the tips of the pointed filaments have a height of about 4 mm, when viewed in a latitudinal direction.

23. An electric toothbrush comprising a brush head with a bristle carrier which can be set in motion and in which bristles are anchored, the bristle carrier being capable of performing a pivoting movement about a pivoting axis running substantially in the longitudinal direction of the brush head, with a maximum pivoting angle, and wherein at least part of the bristles are pointed filaments, which are grouped together in clusters wherein the clusters are at least partially grouped together in rows which run transversely to the pivoting axis, wherein the brush head is driven in such a way that the bristles perform at least 1000 movements per minute.

24. An electric toothbrush comprising a brush head with a bristle carrier which can be set in motion and in which bristles are anchored, the bristle carrier being capable of performing a pivoting movement about a pivoting axis running substantially in the longitudinal direction of the brush head, with a maximum pivoting angle, and wherein at least part of the bristles are pointed filaments, which are grouped together in clusters wherein the clusters are at least partially grouped together in rows which run transversely to the pivoting axis, wherein at least 80% of the tips of the pointed filaments have a height of about 4 mm, when viewed in a latitudinal direction.

25. An electric toothbrush comprising a brush head with a bristle carrier which can be set in motion and in which bristles are anchored, the bristle carrier being capable of performing a pivoting movement about a pivoting axis running substantially in the longitudinal direction of the brush head, with a maximum pivoting angle, and wherein at least part of the bristles are pointed filaments, which are grouped together in clusters wherein the clusters are at least partially grouped together in rows which run transversely to the pivoting axis, wherein during the operation of the electric toothbrush, the tips of the pointed filaments cover at most a path $d_{max}=3$ mm.

* * * * *